United States Patent
Schlummer et al.

(10) Patent No.: US 7,396,964 B2
(45) Date of Patent: Jul. 8, 2008

(54) ENANTIOMERICALLY ENRICHED 2-BUTANOL

(75) Inventors: Björn Schlummer, Leverkusen (DE); Martin Stürmann, Leverkusen (DE)

(73) Assignee: LANXESS Deutschland GmbH, Leverkusen (DE)

( * ) Notice: Subject to any disclaimer, the term of this patent is extended or adjusted under 35 U.S.C. 154(b) by 154 days.

(21) Appl. No.: 10/932,423

(22) Filed: Sep. 2, 2004

(65) Prior Publication Data

US 2005/0054736 A1    Mar. 10, 2005

(30) Foreign Application Priority Data

Sep. 8, 2003    (DE) ............... 103 41 270

(51) Int. Cl.
C07C 27/00    (2006.01)
C07C 27/18    (2006.01)
C07C 29/00    (2006.01)
C07C 29/10    (2006.01)

(52) U.S. Cl. ..................................... 568/907
(58) Field of Classification Search ............ 568/907
See application file for complete search history.

(56) References Cited

FOREIGN PATENT DOCUMENTS

EP    345243    2/1989

OTHER PUBLICATIONS

Sajiki et al (Chem. Comm. 1999, 1041-1042).*
Basolo et al ("Catalysis Progress in Research," pp. 177-185 (1973).*
T. Ohkuma and R. Noyori, Hydrogenation of Carbonyl groups in Comprehensive Asymmetric Catalysis, 1999, Eds.: E.N. Jacobsen, A. Pfaltz, H. Yamamoto, Springer Verlag, Berlin, Heidelberg, New York, p. 199-246.
S. Itsuno, Hydroboration of Carbonyl groups in Comprehensive Asymmetric Catalysis, 1999, Eds.: E.N. Jacobsen, A. Pfaltz, H. Yamamoto, Springer Verlag, Berlin, Heidelberg, New York, p. 290-315.
H. Sajiki, K. Hattori and K. Hirota, Chem Comm. 1999, 1041-1042.
J. Org. Chem., Bd. 38, Nr. 12, 1973, Seiten 2210-2211, XP001204975, J. Coke and R. Shue, "Nucleophilic Ring Opening of Optically Pure®-(+)-1,2-Epoxybutane. Synthesis of New®-2-Butanol Derivatives".

* cited by examiner

*Primary Examiner*—Yvonne Eyler
*Assistant Examiner*—Kellette Gale
(74) *Attorney, Agent, or Firm*—Michael A. Miller

(57) ABSTRACT

The present invention relates to a process for preparing enantiomerically enriched 2-butanol and to its use.

4 Claims, No Drawings

ENANTIOMERICALLY ENRICHED 2-BUTANOL

The present invention relates to a process for preparing enantiomerically enriched 2-butanol and to its use.

Chiral, enantiomerically pure alcohols are important building blocks in the synthesis of high-added value products such as fine chemicals or pharmaceutical intermediates. The synthesis of chiral, enantiomerically pure alcohols is possible in principle via a multitude of chemical transformations.

For example, T. Ohkuma and R. Noyori, Hydrogenation of Carbonyl groups in Comprehensive Asymmetric Catalysis, 1999, Eds.: E. N. Jacobsen, A. Pfaltz, H. Yamamoto, Springer Verlag, Berlin, Heidelberg, New York, p. 199-247 disclose the enantioselective hydrogenation of ketones with chiral ruthenium catalysts.

In addition, S. Itsuno, Hydroboration of Carbonyl groups in Comprehensive Asymmetric Catalysis, 1999, Eds.: E. N. Jacobsen, A. Pfaltz, H. Yamamoto, Springer Verlag, Berlin, Heidelberg, New York, p. 290-315 disclose the asymmetric reduction of ketones with chiral borane reagents.

However, satisfactory enantiomeric excesses are obtained in either process only when the two substituents on the carbonyl group have highly differing steric demands.

A possible alternative is the separation of racemic 2-alcohols. However, the existing chemical methods always proceed via covalent bonds to a chiral auxiliary which, on completion of separation, has to be removed again from the molecule and thus makes the overall process uneconomic. Moreover, in the case of substituents differing only slightly in their steric properties, as is the case especially for 2-butanol, such separating methods only exhibit low enantioselectivity.

Racemic 2-alkanols may be obtained, for example, by regioselective hydrogenation of terminal epoxides (H. Sajiki, K. Hattori and K. Hirota, Chem. Comm. 1999, 1041-1042).

There is a need to provide a process by which enantiomerically enriched 2-butanol is obtainable in a simple and efficient manner.

A process has now been found for preparing enantiomerically enriched 2-butanol, which is characterized in that enantiomerically enriched 1,2-epoxybutane is reduced with hydrogen in the presence of palladium and/or palladium compounds and a vicinal diamine.

In the context of this invention, the term "enantiomerically enriched 2-butanol" refers to mixtures of the particular (R) and (S) enantiomers in which one enantiomer is present in an enantiomeric excess, also referred to hereinbelow as ee, in comparison to the other enantiomer. This ee value is preferably 90 to 100%, more preferably 98 to 100% and most preferably 99 to 100%, and the term "enantiomerically pure" is also used for the latter range.

The process according to the invention is preferably used to prepare (S)-2-butanol from (R)-1,2-epoxybutane.

In the context of the invention, all radical definitions, parameters and illustrations above and listed hereinbelow, specified in general or within areas of preference, i.e. the particular areas and areas of preference, may be combined as desired.

The process according to the invention is carried out in the presence of palladium and/or palladium compounds. Suitable for this purpose is, for example, elemental palladium such as palladium black or palladium applied to a support. Suitable supports are, for example, activated carbon, graphite, kieselguhr, silica gel, spinels, aluminas, calcium carbonate, magnesium oxide, barium sulphate or else organic support materials.

Also suitable are palladium compounds which are very substantially insoluble in organic solvents, for example those which are obtainable by reacting palladium(0) or preferably palladium(II) compounds with hydroxide.

Preferred palladium(II) compounds are compounds of the formulae (Ia) and (Ib)

$$M_2[Pd(Hal)_4] \qquad (Ia),$$

$$Pd(Hal)_2 \qquad (Ib),$$

in which

M is lithium, sodium, potassium, ammonium or organic ammonium and

Hal is chloride, bromide or iodide.

The hydroxides used are preferably alkali metal or alkaline earth metal hydroxides, preferably alkali metal hydroxides such as sodium hydroxide or potassium hydroxide.

The palladium compounds may be used as such or applied to a support. Suitable supports are the abovementioned materials in the same manner. Before use in the process according to the invention, a reduction, for example with hydrazine, may optionally be effected.

The catalysts used are preferably: palladium applied to a support or palladium compounds which are obtained by reacting compounds of the formula (Ia) and/or (Ib) with hydroxide, applied to a support. Preferred supports are pulverulent activated carbons.

The palladium content of catalysts on supports is uncritical and may be varied within a wide range. In general, catalysts on supports are used whose content based on palladium is between 0.1 and 20% by weight, preferably between 0.5 and 15% by weight.

The amount in which the palladium and/or the palladium compound is used may also be varied within a relatively wide range. In general, the amount of palladium and/or palladium compound is selected in such a way that the molar ratio of palladium to 1,2-epoxybutane used is between 1:1 and 1:100 000, preferably between 1:5 and 1:1000 and more preferably between 1:10 and 1:10 000.

The process according to the invention is also carried out in the presence of vicinal diamine. Preferred vicinal diamines are those of the formula (II)

$$H_2N-CR^1-CR^2-NH_2 \qquad (II)$$

in which $R^1$ and $R^2$ are each independently hydrogen, alkyl or aryl, or $CR^1-CR^2$ as a whole is a 5- to 7-membered cycloalkylene radical.

Alkyl is, for example and with preference, an unbranched, branched, cyclic or acyclic $C_1$-$C_{12}$-alkyl radical which may be either unsubstituted or substituted at least partly by fluorine, chlorine or unsubstituted or substituted aryl. Alkyl is more preferably a branched, cyclic or acyclic $C_1$-$C_{12}$-alkyl radical which is not further substituted.

Aryl is, for example, a carbocyclic aromatic radical having 6 to 18 skeleton carbon atoms or a heteroaromatic radical having 5 to 18 skeleton carbon atoms of which no, one, two or three skeleton carbon atoms per cycle, but at least one skeleton carbon atom in the entire molecule, may be substituted by heteroatoms selected from the group of nitrogen, sulphur and oxygen. The carbocyclic aromatic radicals or heteroaromatic radicals may also be substituted by up to five identical or different substituents per cycle, selected from the group of free or protected hydroxyl, iodine, bromine, chlorine, fluorine, cyano, $C_1$-$C_{12}$-alkyl, for example methyl, ethyl, n-propyl, isopropyl, n-butyl, tert-butyl, cyclohexyl, n-hexyl, n-octyl or isooctyl, $C_6$-$C_{12}$-aryl, for example phenyl, or $C_1$-$C_6$-alkoxy.

Aryl is preferably a carbocyclic aromatic radical having 6 to 18 skeleton carbon atoms which are not further substituted.

$R^1$ and $R^2$ are preferably each identically hydrogen, methyl or phenyl or $CR^1$—$CR^2$ as a whole is cyclohexanediyl or cyclopentanediyl.

A particularly preferred vicinal diamine is ethylenediamine.

The amount of vicinal diamine may be, for example, 0.05 to 100 mol per mole of palladium or palladium compound, preferably 0.1 to 20 mol and most preferably 0.1 to 2.5 mol.

Larger amounts of vicinal diamine are possible but uneconomic.

In one embodiment of the process according to the invention, the palladium on a support, before introduction into the reaction, is admixed with the specified amount of vicinal diamine for at least 30 min, preferably 30 min to 12 hours, and the resulting modified catalyst is dried before use in the process according to the invention.

In an alternative embodiment of the process according to the invention, the compounds of the formula (Ia) or (Ib) are reacted with hydroxide, the resulting product, optionally after washing and optionally after reduction, for example with hydrazine, is admixed initially with the specified amount of vicinal diamine and then with the support for at least 30 min, preferably 30 min to 12 hours, and the resulting modified catalyst is dried before use in the process according to the invention.

In a further alternative embodiment of the process according to the invention, the compounds of the formula (Ia) or (Ib) are reacted with hydroxide in the presence of the support and the resulting product, optionally after washing and optionally after reduction, for example with hydrazine, is admixed with the specified amount of vicinal diamine for at least 30 min, preferably 30 min to 12 hours, and the resulting modified catalyst is subsequently dried before use in the process according to the invention.

In a particularly preferred embodiment of the process according to the invention, the compounds of the formula (Ia) or (Ib) are reacted with hydroxide in the presence of the support and the resulting product, optionally after washing and optionally after reduction, for example with hydrazine, or, alternatively, palladium applied to a support, is used directly for the process according to the invention and vicinal diamine is added to the reaction mixture.

The reaction can be carried out preferably without, but optionally also in, an organic solvent.

Suitable solvents for carrying out the process according to the invention are in particular organic solvents. Suitable organic solvents are, for example, aliphatic, alicyclic or aromatic, optionally halogenated hydrocarbons, for example various benzines, benzene, toluene, xylene, chlorobenzene, dichlorobenzene, various petroleum ethers, hexane, cyclohexane, dichloromethane, chloroform, carbon tetrachloride, alcohols such as methanol, ethanol, n- or isopropanol, or mixtures of such organic solvents.

The reaction temperature may be, for example, 0 to 150° C., preferably 10 to 100° C. and more preferably 20 to 50° C.

The partial hydrogen pressure may be, for example, 0.8 to 200 bar, preferably 5 to 100 bar and more preferably 10 to 50 bar.

In a preferred embodiment, the catalyst is recovered and reused for the process according to the invention. The recovery may be effected, for example, by sedimentation and decantation or filtration. No noticeable loss of activity is observed.

The enantiomerically enriched 2-butanol obtainable in accordance with the invention is especially suitable for preparing fine chemicals, active pharmaceutical ingredients or intermediates thereof Preference is given to (S)-2-butanol.

The advantage of the present invention is that, unexpectedly, the process according to the invention provides a highly regioselective epoxide opening which proceeds without the slightest indication of racemization and thus allows an elegant route to enantiomerically enriched 2-butanol.

EXAMPLES

In all of the examples which follow, the optical purity of the (R)— or (S)-2-butanol is determined by gas chromatography on a chiral column material and reported via the ee value. The term "ratio" describes the ratio between 2-butanol and 1-butanol, the two possible products from the hydrogenation of 1,2-epoxybutane.

Example 1

Preparation of Catalyst A 50.0 g (0.047 mol) of palladium on carbon (10% by weight) are slurried with 93 ml of solution containing 5.65 g (0.094 mol) of 1,2-diaminoethane and 87 ml of water, and dried at 50° C. and a pressure of 200 mbar for 2 h. 53 g of catalyst A are obtained.

Example 2

Preparation of Catalyst B 33.3 g of aqueous $Na_2PdCl_4$ solution (0.047 mol) are made up to 300 ml with water. Afterwards, 150 ml of 1 N sodium hydroxide solution are added. The precipitated solid is washed decantingly with 10 litres of water and the solid is filtered off with suction. The solid is admixed with stirring with 5.65 g (0.094 mol) of 1,2-diaminoethane and the solution which forms is made up to 84 ml with water. After 2 h, 45 g of activated carbon are added and the suspension is dried at 50° C. and a pressure of 200 mbar. 59 g of catalyst B are obtained.

Example 3

Preparation of Catalyst C 30.0 g of $Na_2PdCl_4$ solution (0.042 mol) are made up to 300 ml with water. Afterwards, 135 ml of 1 N sodium hydroxide solution are added. The precipitated solid is washed decantingly with 10 litres of water and the solid is filtered off with suction. The solid is admixed with stirring with 5.09 g (0.085 mol) of 1,2-diaminoethane and the solution which forms is made up to 120 ml with water. After 2 h, the dried catalyst is slurried with this solution and dried at 50° C. and a pressure of 200 mbar. 61.1 g of catalyst C are obtained.

Example 4

Preparation of Catalyst D 45.0 g of activated carbon are suspended in 300 ml of water. The slurry is admixed with 50 ml of solution containing 3.33 g of $Na_2PdCl_4$ solution (0.5 g of palladium) and 47 g of water. After 1 h, 10% sodium hydroxide solution is used to set a pH of 8-9. After 2 h, the catalyst is washed on the suction filter to free it of chloride and to neutrality. The solid is then dried at 110° C. and a pressure of 200 mbar.

The catalyst is slurried with 120 ml of solution containing 5.65 g (0.094 mol) of 1,2-diaminoethane and 115 ml of water, and dried at 50° C. and a pressure of 200 mbar for 2 h. 59.5 g of catalyst D are obtained.

Example 5

Preparation of Catalyst E 45.0 g of activated carbon are suspended in 300 ml of water. The slurry is admixed with 50 ml of solution containing 33.3 g of $Na_2PdCl_4$ solution (5.0 g of palladium) and 17 g of water. After 1 h, 10% sodium hydroxide solution is used to set a pH of 8-9. After 2 h, the suspension is reduced with 33 ml of hydrazine hydrate. The catalyst is washed on the suction filter to free it of chloride and to neutrality. The solid is then dried at 110° C. and a pressure of 200 mbar.

The catalyst is slurried with 120 ml of solution containing 5.65 g (0.094 mol) of 1,2-diaminoethane and 115 ml of water, and dried at 50° C. and a pressure of 200 mbar for 2 h. 57.3 g of catalyst E are obtained.

Examples 6-13

General Procedure A for Hydrogenating (R)-1,2-epoxybutane 1 equivalent of (R)-1,2-epoxybutane is dissolved in the specified amount of an organic solvent and introduced into a suitable autoclave. 10% by weight (relative to the substrate) of the palladium catalyst used are added. The autoclave is sealed and the desired hydrogen pressure is set. The reaction mixture is hydrogenated at the temperature specified.

After the end of the reaction, the autoclave is decompressed and the catalyst filtered off using Celite. The chemical and optical purity of the thus obtained filtrate, and also the conversion are determined by means of gas chromatography.

Example 6

Hydrogenation with Catalyst A

| (R)-1,2-Epoxybutane [g]/[mmol] | Catalyst [g] | Solvent | ml | P [bar] | T [° C.] | t [h] | Ratio | ee (S) [%] | Conversion [%] |
|---|---|---|---|---|---|---|---|---|---|
| 0.29 (4.0) | 0.029 | MeOH | 8 | 5 | 25 | 24 | 100:0 | 100 | 20.4 |
| 3.35 (46.5) | 0.335 | — | — | 5 | 25 | 24 | 100:0 | 100 | 19.6 |
| 3.35 (46.5) | 0.335 | — | — | 10 | 25 | 24 | 100:0 | 100 | 33.4 |
| 45.0 (624) | 4.50 | — | — | 50 | 25 | 24 | 99:1 | 100 | 99.2 |

Example 7

Hydrogenation with Catalyst B

| (R)-1,2-Epoxybutane [g]/[mmol] | Catalyst [g] | Solvent | ml | P [bar] | T [° C.] | t [h] | Ratio | ee (S) [%] | Conversion [%] |
|---|---|---|---|---|---|---|---|---|---|
| 0.29 (4.0) | 0.029 | MeOH | 8 | 5 | 25 | 24 | 100:0 | 100 | 3.7 |
| 3.35 (46.5) | 0.335 | — | — | 5 | 25 | 24 | 100:0 | 100 | 14.1 |
| 3.35 (46.5) | 0.335 | — | — | 10 | 25 | 24 | 100:0 | 100 | 13.3 |

Example 8

Hydrogenation with Catalyst C

| (R)-1,2-Epoxybutane [g]/[mmol] | Catalyst [g] | Solvent | ml | P [bar] | T [° C.] | t [h] | Ratio | ee (S) [%] | Conversion [%] |
|---|---|---|---|---|---|---|---|---|---|
| 0.29 (4.0) | 0.029 | MeOH | 8 | 5 | 25 | 24 | 100:0 | 100 | 13.4 |
| 3.35 (46.5) | 0.335 | — | — | 5 | 25 | 24 | 100:0 | 100 | 13.0 |

Example 9

Hydrogenation with Catalyst D

| (R)-1,2-Epoxybutane [g]/[mmol] | Catalyst [g] | Solvent | ml | P [bar] | T [° C.] | t [h] | Ratio | ee (S) [%] | Conversion [%] |
|---|---|---|---|---|---|---|---|---|---|
| 0.29 (4.0) | 0.029 | MeOH | 8 | 5 | 25 | 24 | 99:1 | 100 | 42.0 |
| 3.35 (46.5) | 0.335 | — | — | 5 | 25 | 24 | 99:1 | 100 | 72.1 |
| 3.35 (46.5) | 0.335 | — | — | 5 | 25 | 24 | 99:1 | 100 | 85.7 |

Example 10

Hydrogenation with Catalyst E

| (R)-1,2-Epoxybutane [g]/[mmol] | Catalyst [g] | Solvent | ml | P [bar] | T [° C.] | t [h] | Ratio | ee (S) [%] | Conversion [%] |
|---|---|---|---|---|---|---|---|---|---|
| 0.29 (4.0) | 0.029 | MeOH | 8 | 5 | 25 | 24 | 100:0 | 100 | 6.6 |
| 3.35 (46.5) | 0.335 | — | — | 5 | 25 | 24 | 100:0 | 100 | 1.7 |

Example 11

Hydrogenation with Palladium on Carbon (10% by Weight)

| (R)-1,2-Epoxybutane [g]/[mmol] | Catalyst [g] | Solvent | ml | P [bar] | T [° C.] | t [h] | Ratio | ee (S) [%] | Conversion [%] |
|---|---|---|---|---|---|---|---|---|---|
| 0.29 (4.0) | 0.029 | MeOH | 8 | 5 | 25 | 24 | 88:12 | 100 | 92.9 |

Example 12

Hydrogenation with Palladium on Carbon (10% by Weight) with the Addition of 1,2-diaminoethane in Hydrogenation without Solvent:

| (R)-1,2-Epoxybutane [g]/[mmol] | Catalyst [g] | 1,2-Diaminoethane [g] | P [bar] | T [° C.] | t [h] | Ratio | ee (S) [%] | Conversion [%] |
|---|---|---|---|---|---|---|---|---|
| 3.35 (46.5) | 0.335 | — | 5 | 25 | 24 | 89:11 | 100 | 100.0 |
| 3.35 (46.5) | 0.335 | 0.020 | 10 | 25 | 24 | 99:1 | 100 | 95.8 |
| 3.35 (46.5) | 0.335 | 0.020 | 10 | 50 | 24 | 98:2 | 100 | 99.2 |
| 3.35 (46.5) | 0.335 | 0.040 | 10 | 50 | 24 | 98:2 | 100 | 98.4 |
| 3.35 (46.5) | 0.335 | 0.010 | 10 | 25 | 24 | 98:2 | 100 | 97.8 |
| 3.35 (46.5) | 0.335 | 0.010 | 10 | 50 | 24 | 97:3 | 100 | 98.6 |
| 3.35 (46.5) | 0.335 | 0.005 | 10 | 25 | 24 | 98:2 | 100 | 96.9 |

The invention claimed is:

1. Process for preparing enantiomerically enriched 2-butanol, comprising reducing enantiomerically enriched 1,2-epoxybutane with hydrogen in the presence of palladium compounds and a vicinal diamine wherein the palladium compounds are compounds selected from the group consisting of formula (Ia) and formula (Ib)

$$M_2[Pd(Hal)_4] \quad (Ia),$$

$$Pd(Hal)_2 \quad (Ib)$$

in which

M is lithium, sodium, potassium, ammonium or organic ammonium and

Hal is chloride, bromide or iodide wherein the palladium compounds are formed by reacting formula (Ia) and/or formula (Ib) with hydroxide in the presence of a support thereby forming a resulting product wherein the resultingnroduct com rises the palladium compound applied to the support, and wherein the resulting product and the vicinal diamine are added directly to the enantiomerically enriched 1,2-epoxybutane.

2. The process according to claim 1 wherein the resulting product is washed prior to adding to the enantiomerically enriched 1,2-epoxybutane.

3. The process according to claim 1 wherein the resulting product is reduced prior to adding to the enantiomerically enriched 1,2-epoxybutane.

4. The process according to claim 3 wherein the reduction is with hydrazine.

* * * * *